United States Patent [19]

Beck et al.

[11] Patent Number: 5,714,602
[45] Date of Patent: Feb. 3, 1998

[54] PROCESS FOR THE PRODUCTION OF XYLITOL

[75] Inventors: Roland Herwig Freidrich Beck, Everberg; Myriam Elseviers, Kampenhout; Sonia Marianne Jeannine Coomans, Vilvoorde, all of Belgium

[73] Assignee: Cerestar Holding B.V., Sas van Gent, Netherlands

[21] Appl. No.: 568,601

[22] Filed: Dec. 5, 1995

[30] Foreign Application Priority Data

Dec. 6, 1994 [GB] United Kingdom ............ 9424567

[51] Int. Cl.$^6$ ............ C07H 1/00; C13K 13/00; C07C 29/00; C07C 29/14
[52] U.S. Cl. .................. 536/124; 568/863; 568/852
[58] Field of Search .................. 536/124; 568/863, 568/852

[56] References Cited

U.S. PATENT DOCUMENTS

| | | | |
|---|---|---|---|
| 2,868,847 | 1/1959 | Boyers | 568/863 |
| 3,755,294 | 8/1973 | Walon | 536/124 |
| 4,156,076 | 5/1979 | Dahlgren | 536/124 |
| 4,355,158 | 10/1982 | Wolf et al. | 544/251 |

FOREIGN PATENT DOCUMENTS

93/19030  9/1993  WIPO.

OTHER PUBLICATIONS

Berichte der Deutschen Chemischen Gesellschaft, vol. 32, 27 Feb. 1899 Weinheim, DE, pp. 550–560, O.Ruff: "D--Und r--Arabinose" pp. 553–554.

Journal of the American Chemical Society, vol. 56, No. 7, 5 Jul. 1934 Washington, DC, US, pp. 1632–1633, R.C. Hockett, et al: "Improvements in the preparaton of d--arabinose from calcium gluconate".

Journal of the American Chemical Society, vol. 81, No. 19, 16 Oct. 1959, Washington DC, US, pp. 5190–5192, R.L. Whistler et al. "Preparation of D--arabinose from D--glucose with hypochlorite".

Primary Examiner—John Kight
Assistant Examiner—Everett White
Attorney, Agent, or Firm—Cushman Darby & Cushman IP Group of Pillsbury Madison & Sutro, LLP

[57] ABSTRACT

The present invention discloses a method of producing a pentitol from a hexaldonic acid. The hexaldonic acid is decarboxylated for example in the presence of sodium hypochlorite or hydrogen peroxide. After hydrogenation and optionally isomerisation the desired pentitol, which is obtained in high yield, can be purified. The present invention starts from gluconic acid in free or salt form or as a lactone, xylitol is the final product.

7 Claims, 1 Drawing Sheet

PROCESS FOR THE PRODUCTION OF XYLITOL

BACKGROUND OF THE INVENTION

1. Field of the Invention

The present invention relates to a method for producing a pentitol from a hexaldonic acid. More particularly, the present invention relates to a method for producing xylitol starting from gluconic acid.

2. Description of the Related Art

At present, xylitol is mainly produced on an industrial scale by hydrogenating xylose. Xylose is obtained from xylan such as, for example, through hydrolysis. Xylan containing sources, such as almond shells, corn cobs or birch wood, are used as starting materials. The hydrolysis process suffers from the disadvantages of low yield and low product purity. Extensive purification has to be performed on the hydrolysis product. That is, ion-exchange treatment to remove the acid used for hydrolysis and color, and crystallization to remove the other hemicellulosic sugars also formed during hydrolysis are used in the purification. The purification is required to make the product suitable for application in food.

Other disadvantages relate to waste production. The processing of 12–13 kilograms almond shells required to obtain 1 kilogram of crystalline xylitol produces about 11–12 kilograms of solid waste.

Recently, methods have been described in which xylitol is produced starting from other hexoses. In particular, D-glucose, D-galactose, D-fructose or L-sorbose were used as starting material. In a first step the hexose is subjected to a chain shortening reaction which yields a $C_5$-intermediate. The second basic reaction step (which may be actually more than one step) is the conversion of the $C_5$-intermediate into xylitol.

European patent applications EP-A-0 403 392 and EP-A-0 421 882 (both Roquette Frères) disclose a process in which glucose is fermented to D-arabinitol by an osmophilic yeast. Subsequently, the arabinitol ($C_5$-intermediate) is converted by bacteria (Acetobacter, Gluconobacter or Klebsiella) into D-xylulose. The xylulose is then isomerized by glucose (xylose) isomerase into a xylose/xylulose mixture and either directly hydrogenated or hydrogenated after prior enrichment of xylose.

According to the PCT patent application WO 93/19030, glucose, fructose, galactose or mixtures thereof (obtained through hydrolysis of the disaccharides sucrose and lactose) are oxidatively decarboxylated to give alkali arabinonate and lyxonate, respectively. These aldonic acids are the $C_5$-intermediates, which are transformed into xylitol via arabinitol (=lyxitol). When L-sorbose is used as a starting material in this process L-xylonate is obtained, which can be directly hydrogenated to xylitol.

Other well known chemical methods for xylitol production involve protection group chemistry. Due to a lack of commercial interest these methods are not considered in detail here (Helv.Chim.Acta 58, 1975,311).

Several purely microbiological pathways have also been published. However none of them can compete economically because the overall yield is too low.

Therefore, a need exists for a process for producing xylitol in which the starting material is readily available and the amount of waste product formed is reduced.

A need also exists for an economically valuable method of producing pentitols, especially xylitol, with a low level of impurities, using a reaction sequence giving easily obtainable intermediates, and which are easily refined according to available methods.

SUMMARY AND OBJECTS OF THE INVENTION

The present invention provides a method responding to these needs.

The present method for producing xylitol from gluconic acid, whereby the acid is free, or in the form of its salt or the corresponding lactone, comprises the following steps:

a. decarboxylating gluconic acid, whereby the acid is free, or in the form of its salt or the corresponding lactone, to yield an intermediate consisting mainly of arabinose;

b. hydrogenating the arabinose in the presence of a catalyst to give the corresponding pentitol, e.g., arabinitol;

c. catalytically isomerizing the arabinitol to a xylitol-containing pentitol mixture;

d. separating xylitol from the pentitol mixture to obtain a residual pentitol mixture; and e. optionally, recycling the residual pentitol mixture to the isomerization step(c).

Starting with gluconic acid the method of the present invention gives a high yield of xylitol. The yield is preferably above 60% and more preferably is above 70%. Yields as high as 77% have been obtained. The xylitol obtained can further be purified according to standard methods.

DETAILED DESCRIPTION OF THE INVENTION

Figure 1:
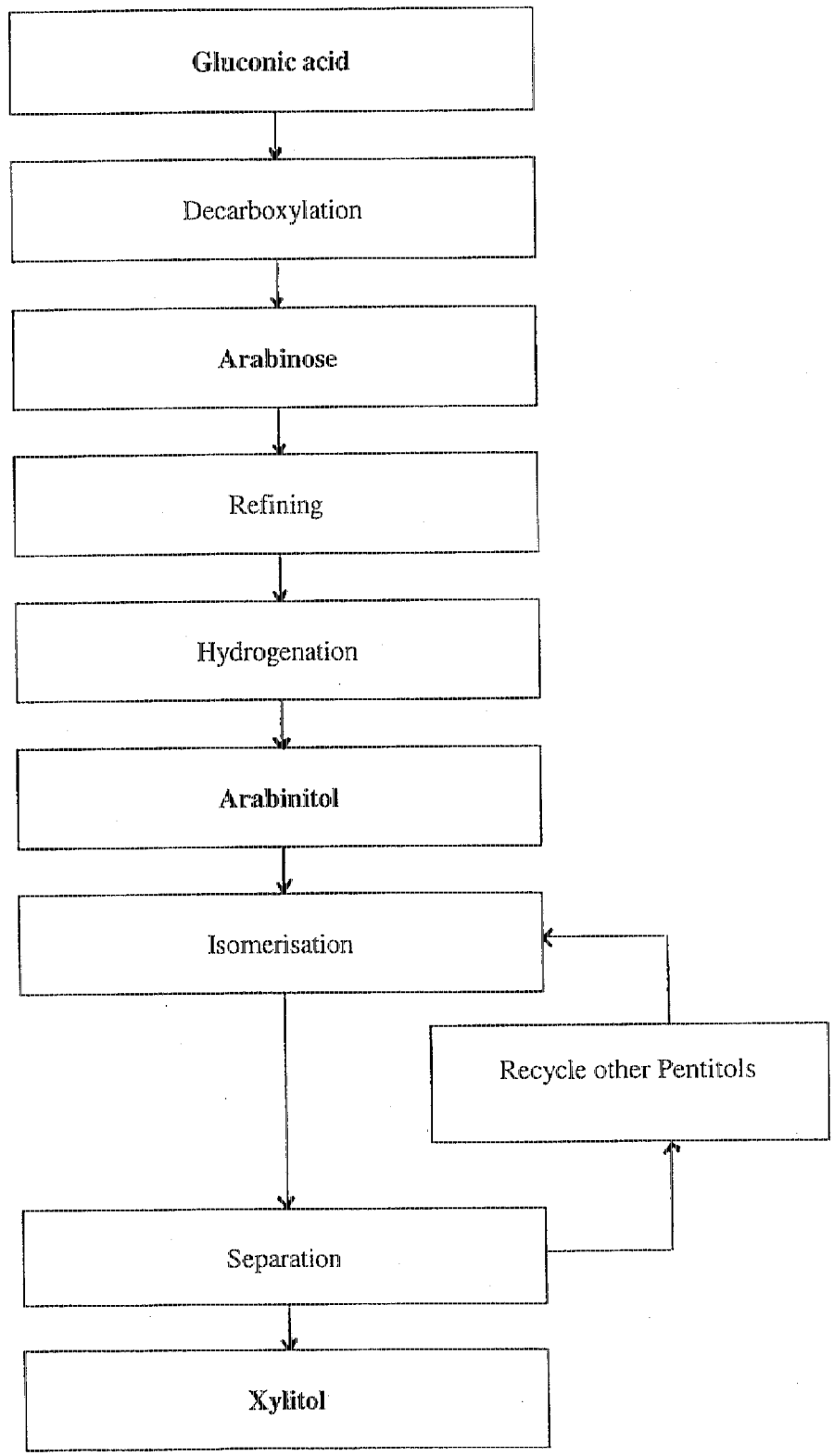
FIG. 1 schematically illustrates an embodiment according to the present invention.

The present invention can be summarized as follows. The starting material is gluconic acid, whereby the acid is free, or in the form of its salt or the corresponding lactone. In the examples illustrating the present invention, sodium gluconate and glucono-delta-lactone have been used as starting materials. Gluconic acid can be obtained, for example, through catalytic oxidation or through fermentation of glucose.

The decarboxylating step (a) to yield arabinose can be according to methods known in the art. A well known method is the one described by Ruff in *Berichte der Deutschen Chemischen Gesselschaft.*, 32 (1899) 553–554. An improved method for the production of arabinose is described in Hockett et al., *J. Amer. Chem. Soc.*, 56 (1934) 1632–1633. A further method is described in Whistler et al., *J. Amer. Chem. Soc.*, 81 (1959) 5190–5192.

The gluconic acid is converted to arabinose. This conversion is performed in water and can, for example, be effectuated by the following two kinds of reagents: A) sodium hypochlorite or an organic hypohalite source, for example, N-chlorosuccinimide (in situ formation of hypochlorite); and B) hydrogen peroxide in the presence of catalytic amounts of $Fe^{+++}$ or $Cu^{++}$.

An advantage of the use of arabinose as an intermediate is that it can easily be purified by ion-exchange refining. The ion-exchange refining, which is a purification method, would not be possible with arabinonic acid as an intermediate.

The obtained non-ionic arabinose is hydrogenated, in step (b), under mild reaction conditions, with respect to hydrogen pressure and temperature, using well known hydrogenation catalysts to give arabinitol. Suitable catalysts are ruthenium or nickel. In particular, supported ruthenium catalysts, for example, ruthenium-on-carbon are used. As to nickel, Raney nickel can be used. The hydrogenation is routinely performed at temperatures between 70° C. and 150° C. and at pressures between 0.1 and 10 MPa.

The obtained D-arabinitol is subjected to catalytic isomerization in step (c). D-arabinitol is treated at elevated temperatures, preferably above 100° C., and elevated pressures of hydrogen gas, preferably above 1 MPa, in the presence of hydrogenation/dehydrogenation catalysts. These catalysts are, for instance, ruthenium, copper, palladium, platinum, rhodium, cobalt and nickel based catalysts, and, in general, metal oxides and mixtures thereof.

The polyol isomerization is performed at distinctly different pH levels, and the addition of alkali or acid has an influence on the thermodynamic equilibrium of the pentitol mixture. The isomerization reaction results in a product containing xylitol, ribitol and D,L-arabinitol. Xylitol is present in these mixtures in more than 10%, and is preferably present in more than 20%. This reaction product further contains some lower alditols, such as tetritols and triitols, adding up to maximum of 10%, and preferably only to 5%.

The isomerization mixture is optionally refined, such as being subjected to chromatography. It has been found that subjecting the isomerization mixture to chromatography on cationic resin material yields xylitol with a purity in excess of 95%. By preference, the mixture is first demineralized and subsequently subjected to chromatography.

The refining is suitably performed using a strong cation exchange resin, such as, for instance, Duolite A 368. This process is preferably repeated. On a plant scale, the chromatography is performed using suitable equipment obtainable for example from Mitsubishi with Diaion UBK-555 resin (in $Ca^{2+}$ form). Separation methods have been extensively described in, for example, EP-A-0 403 392, and the references cited therein (page 5, line 39 to page 6, line 21).

The other pentitols are optionally recycled to the polyols isomerization, which results in an increased overall yield.

The xylitol can also further be purified by crystallization.

The advantage of this process in comparison with earlier described processes, such as disclosed in PCT International Application WO 93/19030, is that well established unit operations can be used for the refining of arabinose which would not be possible with arabinonic acid (classical syrup refining) and that known techniques and equipment for the hydrogenation (classical polyol hydrogenation) can be used. An advantage compared with methods such as those described in EP-A-0 403 392 and EP-A-0 421 882 is that although the reaction sequence up to arabinitol is also mentioned in these disclosures, the present invention gives a much shorter reaction sequence from arabinitol towards the desired pentitol; xylitol.

Schematically the method of the present invention is illustrated in FIG. 1.

The invention will be further illustrated in more detail in the following non-limiting examples.

EXAMPLE 1

218 g Sodium gluconate (1 Mol) was dissolved in 800 ml demineralized water and the pH brought to 5.0. The solution was brought to 55° C. and 1068 ml sodium hypochlorite (16% w/v) was added continuously over a period of 15 minutes, while keeping the pH value between 4.9 and 5.1 using diluted hydrochloric acid. After all the hypochlorite had been added, the reaction was allowed to continue for 30 minutes. No residual active chlorine was detectable after this period.

After demineralization and refining, the product had the following composition: 96% D-arabinose, 2% D-glucose, 2% unknown sugars (isomerization products or $C_4$-sugars). The total weight yield of the above demineralized product was 137.5 g, of which 132 g was D-arabinose (88% of theory).

The arabinose syrup was hydrogenated on Raney Nickel (5% catalyst on total dry substance) applying a hydrogen pressure of 4 MPa at a temperature of 110° C. Hydrogenation was completed within 2.5 hours. The reducing sugar amount was lower than 0.1% as measured by DE measurement. Isomerization of the formed D-arabinitol was performed by increasing the pH value in the hydrogenation autoclave to 9 to 10. After 6 hours at 170° C. the reaction was terminated. The obtained demineralized isomerizate had the following pentitol composition: D,L-arabinitol (71%), ribitol (13%), xylitol (16%).

The xylitol was separated by chromatography on an cation exchange resin in the calcium form, yielding xylitol with a purity of greater than 95%. The arabinitol and ribitol were recycled to the isomerization step.

The obtained xylitol was crystallized.

EXAMPLE 2

178 g glucono-delta-lactone (1 Mol) was dissolved in 800 ml demineralized water and the pH brought to 5.5. Ferric sulfate (5.4 g) was added as a catalyst. The solution was brought to 65° C. and 204 ml hydrogen peroxide (30% w/v) was added in 4 portions with an interval of 1 hour, while keeping the pH value between 5.4 and 5.6 through the addition of diluted acetic acid. After all the hydrogen peroxide had been added, the reaction was allowed to continue for 1 hour. No residual hydrogen peroxide was detectable after this period.

After demineralization and refining the product had the following composition: 82% D-arabinose, 6% D-glucose, 12% unknown sugars (isomerization products or $C_4$-sugars). The total weight yield of above demineralized product was 128 g, of which 105 g was D-arabinose (70% of theory).

The arabinose syrup was hydrogenated using a ruthenium catalyst (2% catalyst on total dry substance), which was supported on active carbon (5% Ru on carbon). Phosphoric acid (1% on total dry substance) was added to the arabinose syrup. The reaction temperature was 150° C. and the hydrogen pressure was 4 MPa. Within 2 hours the residual reducing sugar content was lower than 0.1% as measured by DE measurement and the isomerization proceeded to a sufficient level. The addition of phosphoric acid induces isomerization during the hydrogenation. The obtained hydrogenated syrup had the following composition: 81% total pentitols (of which 21% xylitol, 14% ribitol, 65% D,L-arabinitol) and 19% tetritols and hexitols.

The xylitol was recovered as in Example 1.

EXAMPLE 3

178 g glucono-delta-lactone (1 Mol) was dissolved in 800 ml demineralized water and the pH brought to 7.5. Copper (II) sulfate (3.4 g) was added as a catlyst. The solution was brought to 65° C. and 362.6 ml hydrogen peroxide (30% w/v) was added in 7 portions with an interval of 1 hour, while keeping the pH value between 7.4 and 7.6 through the addition of diluted sodium hydroxide. After all the hydrogen peroxide had been added, the reaction was allowed to continue for 1 hour. No residual hydrogen peroxide was detectable after this period.

After demineralization and refining the product had the following composition: 85% D-arabinose, 8% D-glucose, 7% unknown sugars (isomerization products or $C_4$-sugars). The total weight yield of above demineralized product was 137 g, of which 117 g was D-arabinose (78% of theory).

The arabinose syrup was hydrogenated on a ruthenium catalyst (4% catalyst on total dry substance), which was supported on active carbon (5% Ru on carbon). The reaction temperature was 135° C. and the hydrogen pressure was 4 MPa. Within 1 hour the residual reducing sugar content was lower than 0.1% as measured by DE measurement. The hydrogenated syrup had the following composition: 84% D-arabinitol and 16% tetritols and hexitols. Phosphoric acid (1% on total dry substance) was added to the hydrogenated syrup and isomerization was performed for 3 hours at a hydrogen pressure of 40 bar and a temperature of 150° C. The obtained isomerized, hydrogenated syrup had the following composition: 83% total pentitols (of which 29% xylitol, 21% ribitol, 50% D,L-arabinitol) and 17% tetritols and hexitols.

The xylitol was recovered as in Example 1.

We claim:

1. A method of producing xylitol from gluconic acid wherein the acid is in free form or in the form of a salt or the corresponding lactone which comprises the following steps a. decarboxylating the gluconic acid to give an intermediate consisting mainly of arabinose, b. hydrogenating the arabinose in the presence of a catalyst to give the corresponding pentitol, arabinitol, c. catalytically isomerizing the arabinitol to a xylitol-containing pentitol mixture, d. separating xylitol from the pentitol mixture to obtain a residual pentitol mixture, and e. optionally recycling of the residual pentitol mixture to step (c).

2. A method according to claim 1, wherein the decarboxylation is performed using a hypochlorite.

3. A method according to claim 1, wherein the decarboxylation is performed using hydrogen peroxide in the presence of a catalytic amount of $Fe^{3+}$ or $Cu^{2+}$.

4. A method according to claim 1, wherein the hydrogenation is performed in the presence of Ruthenium or Raney-Nickel as a catalyst.

5. A method according to claim 1, wherein the isomerization is performed in the presence of a hydrogenation/dehydrogenation catalyst promoted by the addition of an alkali or an acid.

6. A method according to claim 1, wherein the separation of xylitol is performed using a cationic resin.

7. A method according to claim 1, wherein the xylitol from step (d) is crystallized.

* * * * *